US00PP22002P2

(12) United States Plant Patent
Sills et al.

(10) Patent No.: US PP22,002 P2
(45) Date of Patent: Jul. 5, 2011

(54) BLACKBERRY PLANT NAMED 'DRISBLACKTWO'

(50) Latin Name: ***Rubus* L. subgenus *Rubus***
Varietal Denomination: DrisBlackTwo

(75) Inventors: Gavin R. Sills, Watsonville, CA (US); Stephen B. Moyles, Soquel, CA (US); Andrea M. Pabon, Watsonville, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 12/655,259

(22) Filed: Dec. 28, 2009

(51) Int. Cl.
*A01H 5/00* (2006.01)

(52) U.S. Cl. ..... Plt./203

(58) Field of Classification Search ..... Plt./203
See application file for complete search history.

*Primary Examiner* — Susan B McCormick Ewoldt
(74) *Attorney, Agent, or Firm* — Jondle & Associates, P.C.

(57) ABSTRACT

This invention relates to a new and distinct variety of Blackberry plant named 'DrisBlackTwo', which is primarily characterized by spineless canes, medium-sized, ovate fruit that matures to a black color and having a medium time of bud burst, is disclosed.

4 Drawing Sheets

Genus and species: *Rubus* L. subgenus *Rubus*.
Variety denomination: 'DrisBlackTwo'.

BACKGROUND OF THE NEW PLANT

The present invention relates to a new and distinct Blackberry cultivar designated 'DrisBlackTwo' and botanically known as *Rubus* L. subgenus *Rubus*. This new Blackberry variety was discovered in Santa Cruz County, Calif. in July 2004 and originated from a cross between the female parent Blackberry plant 'BH936-6' (unpatented) and the male parent Blackberry plant 'Driscoll Cowles' (U.S. Plant Pat. No. 14,780). The original seedling of the new cultivar was asexually propagated at a nursery in Santa Cruz County, Calif. 'DrisBlackTwo' was subsequently asexually propagated and underwent further testing at a nursery in Santa Cruz County, Calif. for five years. The present invention has been found to be stable and reproduce true to type through successive asexual propagations.

SUMMARY OF THE INVENTION

The following are the most outstanding and distinguishing characteristics of this new cultivar when grown under normal horticultural practices in Santa Cruz, Calif.

1. Spineless canes;
2. Medium-sized, ovate fruit that mature to a black color; and
3. Having a medium time of bud burst.

DESCRIPTION OF THE PHOTOGRAPHS

This new Blackberry plant is illustrated by the accompanying photographs, which show the fruit of the plant as well as the canes; the colors shown are as true as can be reasonably obtained by conventional photographic procedures. The photographs are of plants that are 2 years old.

DESCRIPTION OF THE NEW VARIETY

Figure 1:
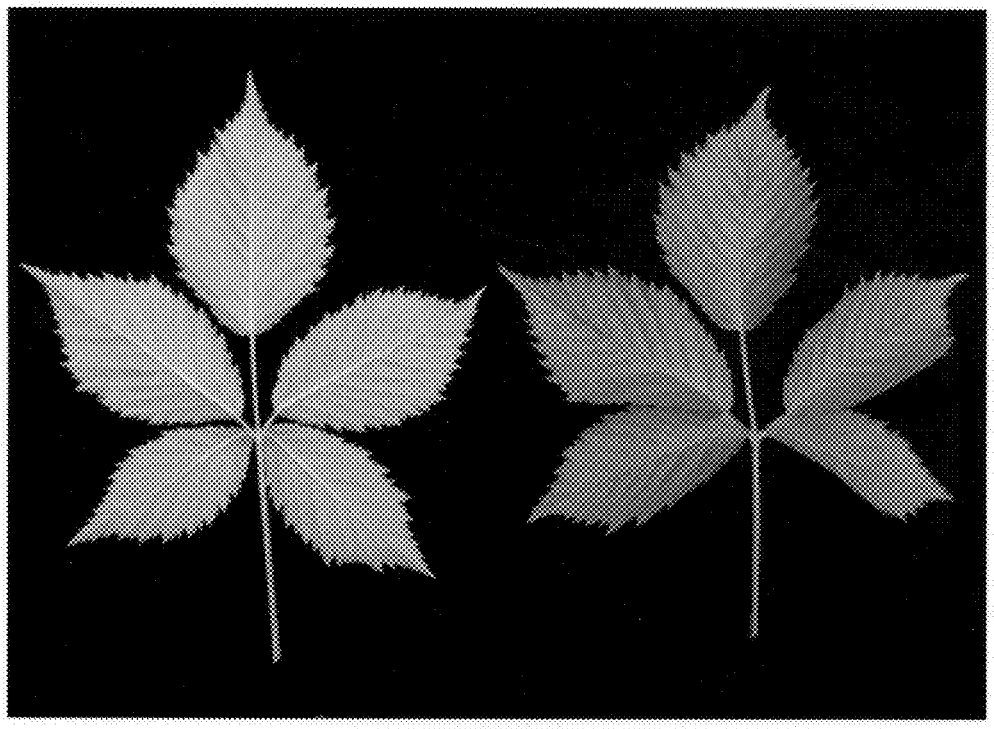
FIG. 1 shows the upper and lower side of the leaves.
Figure 2:
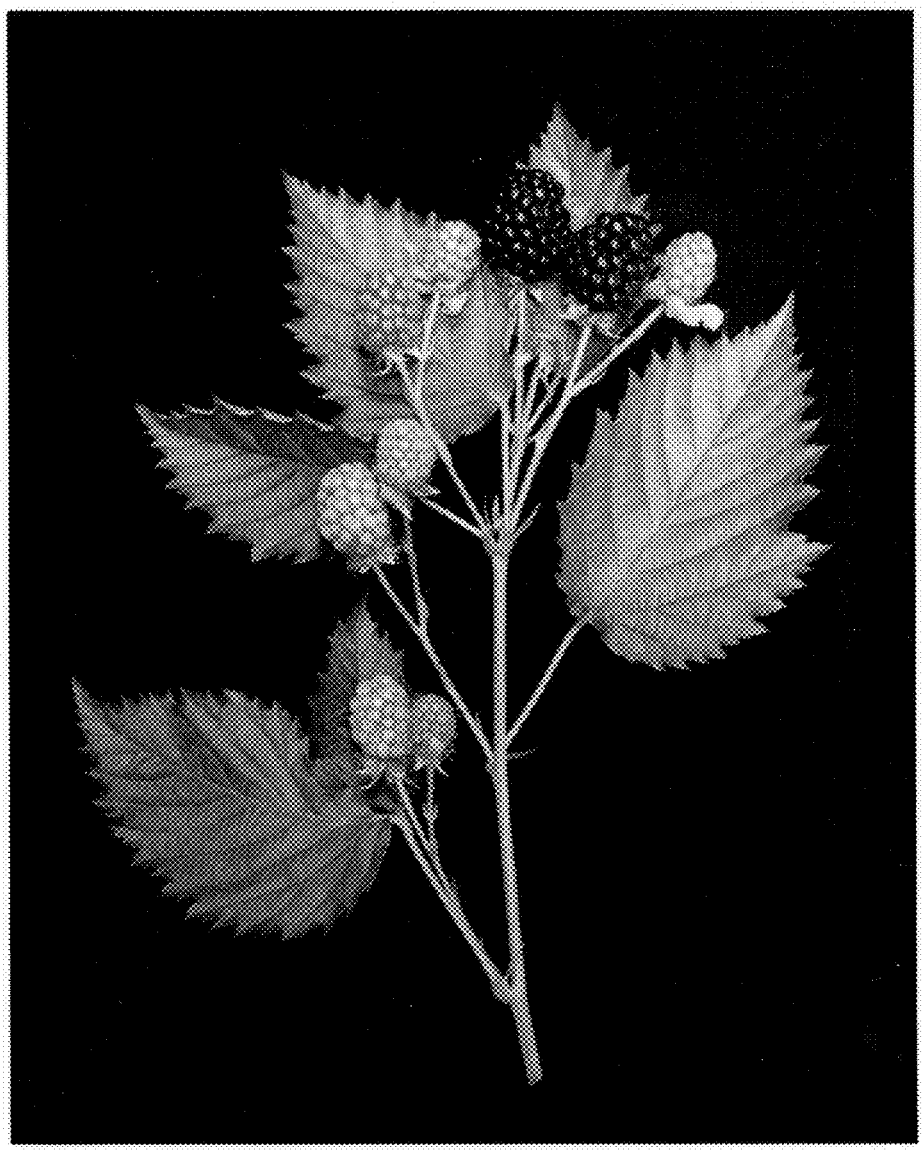
FIG. 2 shows immature fruit at various stages as well as mature fruit.
Figure 3:
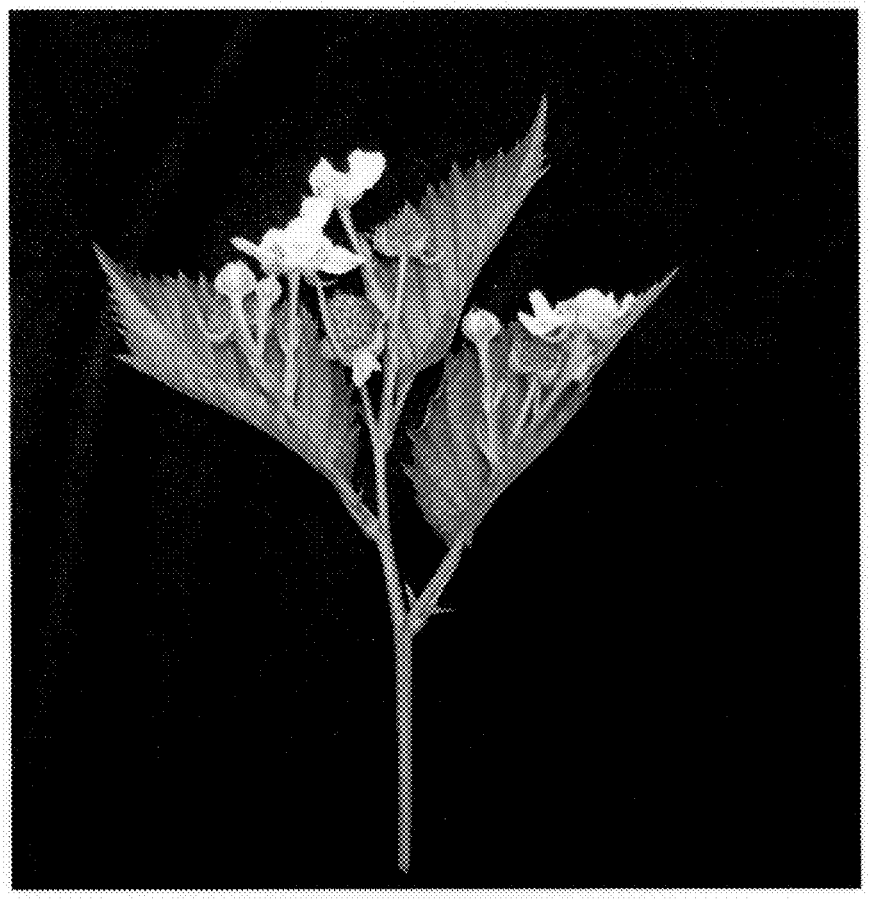
FIG. 3 shows flowers, flower buds and immature fruit.
Figure 4:
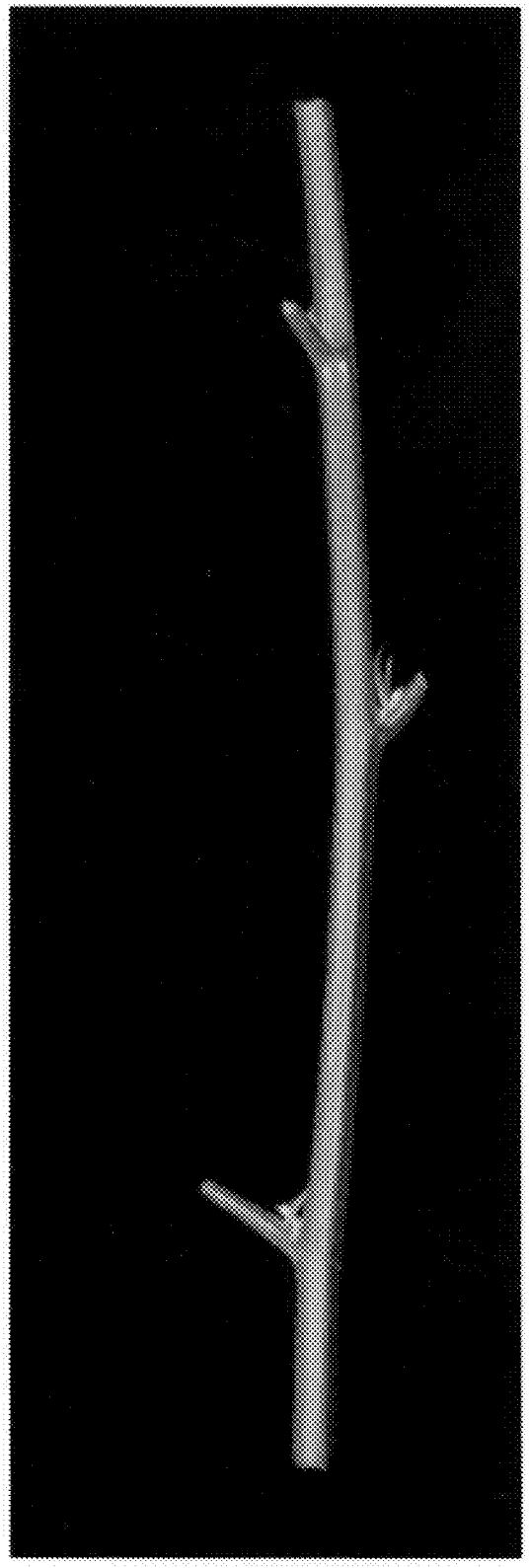
FIG. 4 shows a section of a spineless young cane.

The following description of 'DrisBlackTwo' is based on observations of plants that are 2 years old taken from the 2005 to 2009 growing seasons in Santa Cruz County, Calif. This description is in accordance with UPOV terminology. Color designations, color descriptions, and other phenotypical descriptions may deviate from the stated values and descriptions depending upon variation in environmental, seasonal, climatic and cultural conditions. 'DrisBlackTwo' has not been observed under all possible environmental conditions. Color terminology follows The Royal Horticultural Society Colour Chart, London (R.H.S.) (2001 edition).

DETAILED BOTANICAL DESCRIPTION

Classification:
- *Family.*—Rosaceae.
- *Botanical.*—*Rubus* L. subgenus *Rubus*.
- *Common name.*—Blackberry.
- *Variety name.*—'DrisBlackTwo'.

Parentage:
- *Female parent.*—The blackberry plant 'BH936-6' (unpatented).
- *Male parent.*—The blackberry plant 'Driscoll Cowles' (U.S. Plant Pat. No. 14,780).

Plant:
- *Vigor.*—High.
- *Growth habit.*—Semi-upright.
- *Productivity.*—High.
- *Propagation.*—Tissue culture and root cuttings.
- *Self-fruitfulness.*—Partially self-fruitful.
- *Time of bud burst.*—Medium.

Fruiting:
- *Lateral length.*—Between long and very long.
- *Length* ($4^{th}$ *lateral from tip*) *average cm.*—18.4.
- *Number of fruit per lateral.*—Average: 6.7. Range: 11 to 45.

Shoot:

*Number of young shoots.*—Medium.

*Very young shoots intensity of anthocyanin coloration.*—Between medium and strong.

*Time of young shoot emergence from soil.*—Late.

*Young shoot pigmentation.*—RHS 183A (Dark greyed-purple).

*New cane strength* (*observed full-grown shoot after picking*).—Strong.

*Shoot length* (*cm*).—Average: 380.64 cm. Range: 271.80 cm to 530.00 cm.

*Glaucosity* (*waxy bloom*) (*observed on full-grown shoot after picking*).—Absent.

*Cane cross section* (*from mid cane observed at end of first growing season*).—Rounded to angular.

*Dormant cane color.*—RHS 152A (Medium yellow-green).

*Pubescence on canes.*—Present.

Cane internodal distance (distance between nodes):

*Internodal distance* (*cm*) (*at central ⅓ of cane*).—Average: 10.8 cm. Range: 6.4 cm to 15.2 cm.

Leaves

*Color.*—Upper surface: RHS 147A (Dark yellow-green). Lower surface: RHS 146B (Medium yellow-green).

*Arrangement.*—Compound; whorled (3 or more leaves per node).

*Number of leaflets.*—Sometimes 3, sometimes 5.

*Relief between veins.*—Medium.

*Glossiness.*—Dark.

*Number of leaflets.*—More than three leaflets (on up to 5 out of 10 leaves).

*Cross section profile.*—Concave.

*Petiole.*—Length (cm): Average: 7.1 cm. Range: 5.1 cm to 10.2 cm. Pigmentation of upper surface: Heavy. Pigmentation of upper surface RHS 183A (Dark greyed-purple). Pigmentation of lower surface: Lightly. Pigmentation of lower surface: RHS 146C (Medium yellow-green).

*Stipule.*—Orientation: Erect.

*Overlapping of lateral leaflets.*—Overlapping.

*Terminal leaflet.*—Length: Average: 14.07 cm. Range: 10.8 cm to 17.1 cm. Width: Average: 7.9 cm. Range: 5.7 cm to 10.2 cm. Shape: Ovate. Tip: Acuminate. Base: Cordate. Apex: Truncate. Shape of teeth: Acute. Margin: Doubly serrate. Cross-section: Concave.

*Lateral leaflet* (*basal pair*).—Length of Stalklet (lower pair): Short. Length: Average: 10.9 cm. Range: 8.3 cm to 12.7 cm. Width: Average: 6.1 cm. Range: 4.4 cm to 7.6 cm. Shape: Ovate. Tip: Acuminate. Base: Elliptical. Margin: Doubly serrate. Rachis length between terminal leaflet and adjacent lateral leaflet (cm): Average: 2.0 cm. Range: 0.8 cm to 2.8 cm.

*Overlap of lateral leaflets.*—Yes.

Inflorescence:

*Time of beginning of flowering.*—Late.

*Flower size.*—Small to medium.

*Flower diameter.*—Average: 3.7 cm. Range: 2.5 cm to 4.4 cm.

*Diameter of calyx relative to corolla.*—Much smaller.

*Spacing of petals* (*observe only on secondary flowers with* 5 *or* 6 *petals*).—Free.

*Flower number* (*at* 3$^{rd}$ *node from tip of lateral*).—Average: 7. Range: 4 to 8.

*Petal.*—Length: Average: 2.3 cm. Range: 1.4 cm to 6.8 cm. Width: Average: 1.1 cm. Range: 1.0 cm to 1.8 cm. Color: RHS 65C (Light red-purple). Shape: Oval. Apex: Rounded. Margin: Entire. Base: Concave. Length/width ratio (observe on secondary flowers): Much longer than broad.

*Sepal.*—Margin: Entire. Color: RHS 144A (Medium yellow-green).

*Pedicel.*—Anthocyanin coloration: Strong. Length: Short.

Fruit:

*Time of ripening.*—Medium.

*Harvest interval.*—Early June to mid-October.

*Length of harvest season.*—Late to very late.

*Color.*—Immature: RHS 140B (Medium green). Maturing: RHS 46A (Dark red). Mature: RHS 202A (Black).

*Glossiness.*—Strong.

*Shape.*—Ovate.

*Size.*—Medium.

*Length.*—Average: 2.7 cm. Range: 2.5 cm to 2.9 cm.

*Width.*—Average: 2.1 cm. Range: 2.0 cm to 2.3 cm.

*Ratio of length to width.*—Longer than broad.

*Weight* (*g/fruit*).—5.68.

*Soluble solids* (%) (*in Brix*).—11.6.

*Titratable acidity* (% *as citric acid*).—0.90.

*Seed weight* (*g/seed*).—0.0034.

*Number of druplets/fruit.*—92.

*Firmness.*—Firm.

*Yield.*—Between high and very high.

COMPARISON WITH PARENTAL AND COMMERCIAL VARIETIES

'DrisBlackTwo' differs from the female parent 'BH936-6' (unpatented) in that 'DrisBlackTwo' is spineless and has a late to very late harvest season, while 'BH936-6' is a spiny plant that has a mid-late harvest season. Additionally, 'DrisBlackTwo' has a fruit that weighs on average 5.68 g, while fruit of 'BH936-6' weighs on average 6.0 g. Furthermore, 'DrisBlackTwo' has a high fruit yield, while 'BH936-6' has a mediocre fruit yield.

'DrisBlackTwo' differs from the proprietary male parent 'Driscoll Cowles' (U.S. Plant Pat. No. 14,780) in that the fruit of 'DrisBlackTwo' has a high fruit productivity, while 'Driscoll Cowles' has a medium fruit productivity. Additionally, 'DrisBlackTwo' is partially self-fruiting and has a medium time to bud burst, while 'Driscoll Cowles' is fully self-fruiting and has a late time to bud burst.

'DrisBlackTwo' differs from the commercial variety 'Driscoll Thornless Sleeping Beauty' (U.S. Plant Pat. No. 17,983) in that 'DrisBlackTwo' has a semi-upright growth habit, high fruit productivity, is partially self-fruiting and a medium time of bud burst, while 'Driscoll Thornless Sleeping Beauty' has an upright growth habit, moderate fruit productivity, is fully self-fruiting and an early time of bud burst.

We claim:

1. A new and distinct cultivar of Blackberry plant as described and shown herein.

* * * * *